(12) United States Patent
Lee et al.

(10) Patent No.: US 10,932,909 B2
(45) Date of Patent: Mar. 2, 2021

(54) DEVICE FOR TREATING REGURGITATION OF TRICUSPID AND IMPLANTATION METHOD THEREFOR

(71) Applicant: Shanghai Joy Medical Devices Co., Ltd., Shanghai (CN)

(72) Inventors: Shouyan Lee, Rancho Santa Margarita, CA (US); Hongxia Nan, Shanghai (CN)

(73) Assignee: SHANGHAI JOY MEDICAL DEVICES CO., LTD, Shanghai (CN)

( * ) Notice: Subject to any disclaimer, the term of this patent is extended or adjusted under 35 U.S.C. 154(b) by 0 days.

(21) Appl. No.: 16/508,312

(22) PCT Filed: Feb. 7, 2017

(86) PCT No.: PCT/CN2017/073069
§ 371 (c)(1),
(2) Date: Jul. 11, 2019

(87) PCT Pub. No.: WO2018/145249
PCT Pub. Date: Aug. 16, 2018

(65) Prior Publication Data
US 2020/0000592 A1    Jan. 2, 2020

(51) Int. Cl.
*A61F 2/24* (2006.01)
*A61B 17/00* (2006.01)
*A61F 2/07* (2013.01)

(52) U.S. Cl.
CPC ............ *A61F 2/246* (2013.01); *A61F 2/2418* (2013.01); *A61F 2/2427* (2013.01); *A61F 2/2457* (2013.01); *A61F 2/2463* (2013.01); *A61B 2017/00243* (2013.01); *A61F 2/07* (2013.01); *A61F 2/2466* (2013.01);
(Continued)

(58) Field of Classification Search
CPC ....... A61F 2/24–2475; A61F 2250/0015–0017
See application file for complete search history.

(56) References Cited

U.S. PATENT DOCUMENTS 8,002,825 B2 * 8/2011 Letac ................... A61F 2/2412
623/2.14
2006/0052867 A1 3/2006 Revuelta et al.
(Continued)

FOREIGN PATENT DOCUMENTS

CN    102939059    2/2013
CN    106073945    11/2016
(Continued)

*Primary Examiner* — Rebecca S Preston
(74) *Attorney, Agent, or Firm* — Treasure IP Group, LLC (57) ABSTRACT

A device for treating regurgitation of a tricuspid valve (4) is disclosed. The device comprises a tricuspid valve plug (21) capable of compressing and expanding and a tricuspid valve plug fixing device used for anchoring the tricuspid valve-in-plug (21) to an orifice of the tricuspid valve (4). The tricuspid valve plug (21) is provided with an inflow end (42, 52) and an opposite outflow end (47, 57), and a prosthetic valve (50, 70) capable of being opened and closed is disposed in the tricuspid valve plug (21). When the tricuspid valve (4) is dosed, the prosthetic valve (50, 70) is automatically closed, and when the tricuspid valve (4) is opened, the prosthetic valve (50, 70) is automatically opened.

10 Claims, 10 Drawing Sheets

(52) U.S. Cl.
CPC ............... *A61F 2210/0014* (2013.01); *A61F 2230/0017* (2013.01); *A61F 2250/0017* (2013.01); *A61F 2250/0039* (2013.01); *A61F 2250/0069* (2013.01)

(56) References Cited

U.S. PATENT DOCUMENTS

| | | | |
|---|---|---|---|
| 2009/0276040 A1* | 11/2009 | Rowe | A61F 2/2454 623/2.18 |
| 2014/0142691 A1 | 5/2014 | Pouletty | |
| 2016/0120643 A1* | 5/2016 | Kupumbati | A61F 2/2436 623/2.18 |
| 2017/0100241 A1 | 4/2017 | Modine | |
| 2017/0143478 A1* | 5/2017 | Schwartz | A61F 2/2466 |
| 2017/0172737 A1* | 6/2017 | Kuetting | A61F 2/2418 |

FOREIGN PATENT DOCUMENTS

| | | |
|---|---|---|
| WO | 2013173587 | 11/2013 |
| WO | 2015177655 | 11/2015 |

\* cited by examiner

DEVICE FOR TREATING REGURGITATION OF TRICUSPID AND IMPLANTATION METHOD THEREFOR

CROSS REFERENCE TO RELATED APPLICATION

This application is a national stage application of PCT/CN2017/073069, filed on Aug. 16, 2018. The international application is incorporated herein by reference in its entirety.

TECHNICAL FIELD

The present disclosure pertains to the field of cardiovascular medical devices, in particular relates to an implantable device for treating heart valve regurgitation, and method of implanting the same.

BACKGROUND OF THE INVENTION

The mammalian heart contains four chambers, two atriums as chambers for inflow and two ventricles as chambers for blood pump-out. In mammalian hearts, there are four heart valves, which usually allow blood to flow through the heart in only one direction, where the heart valve opens or closes depending on the blood pressure difference across the valve. The four main valves in the heart include mitral valve, as well as tricuspid valve, which are located respectively between the atrium and the ventricle, and are therefore referred to as atrioventricular (AV) valves. Also, there are aortic and pulmonary valves from which aorta or pulmonary artery originates. Mitral and aortic valves are in the left side of the heart, and the tricuspid and pulmonary valves are in the right side of heart. Each valve comprises multiple leaflets, where tricuspid valve has three leaflets. The function of mitral and tricuspid valves is to prevent backflow from the ventricle to the atrium during systole. There are chordae attached to the leaflets and the ventricular wall to hold leaflet in position without prolapse.

Tricuspid regurgitation (TR) is a common heart valve disease, and functional tricuspid regurgitation usually stems from left heart disease such as mitral regurgitation and can be fatal if not treated. Surgical correction of tricuspid regurgitation alone is not common, it is usually remedied when surgically treating left heart diseases, for example mitral valve regurgitation. Severe tricuspid regurgitation will result in the low cardiac output and systemic congestion, which inevitably leads to high mortality and morbidity according to published literature.

At present, the treatments of tricuspid regurgitation can only be remedied by open heart surgery, such as valve annuloplasty, valve leaflet repair, papillary muscle or chordae repair, edge to edge repair etc. Currently, the numbers of patients with moderate and severe tricuspid regurgitation are 1.6 million in the United States, and 5 million China estimated by population. Only 0.5% of the patients are suitable for surgery such as valve annuloplasty. Rest of the patients are usually high risk patients not suitable for surgery. Currently, these high risk patients can only be managed conservatively by medication. Even for surgical treatment, 74% of the patients who received tricuspid valve repair had recurring tricuspid regurgitation after three years. Among the elderly over the age of 54, the incidence of tricuspid regurgitation for males was 14.8% and that of females was 18.4%. There is a lot of evidence showing that moderate to severe tricuspid regurgitation should be treated same time with Mitral valve repair or replacement; if not treated at the time of mitral surgery, the tricuspid regurgitation could rapidly worsen. However, a subsequent surgery always involves high risk and mortality.

Minimally invasive techniques treating tricuspid regurgitation are present in research and development stage, some of the techniques are transcatheter valve annuloplasty, a tricuspid plug, and edge to edge clip. Annuloplasty such as the bicuspidization technique by Mitralign Mitralign system, mimics a surgical approach involving shim implanting and suturing via the jugular vein to convert the tricuspid valve to bicuspid valve; and the TriCinch, involves a placing stainless-steel screw at the anterior-posterior leaflet junction of the tricuspid valve to convert the three leaflet valve to dual leaflets. Although these procedures can theoretically reduce tricuspid regurgitation, there are significant procedural difficulties and results vary. Use of a tricuspid plug is minimally invasive and generally utilizes a solid plug device placed in the orifice of the tricuspid valve leaflets to block the leakage gap thus reduces regurgitation. There are a few types of the tricuspid plug: a balloon plug, uses a bulging fluid/foam-filled balloon cylindrical shape, or a bell-shaped plug. While the plug placed in valve leakage gap can reduce regurgitation since the plug blocks the back flow during systole, it may significantly reduce the effective orifice area of the tricuspid valve during diastole since the plug also restricted the opening; this would result in elevation of venous pressure and reduction of right ventricular function, especially when the diameter of plug is too large.

In order to mitigate the risk of open-heart surgery for high risk patients and redo surgery patients, in order to address procedure complexity of minimally invasive annuloplasty, in order to avoid the stenosis caused by a tricuspid plug, a more effective and less invasive method is desired.

SUMMARY OF THE INVENTION

In view of the above technical problems, the present disclosure of implanting plug device with a prosthetic valve inside the plug at the native tricuspid valve orifice, which can block the tricuspid valve leakage gap during systole. The device also allows maximum blood inflow through the orifice of the prosthetic valve and the native valve during diastole. Therefore, the device in the disclosure provides an effective treatment for tricuspid valve regurgitation without the potential of tricuspid stenosis.

As described above, the present disclosure primarily introduces a device for treating tricuspid regurgitation. The device comprises a compressible and expandable plug, an anchoring device to place the plug in the native tricuspid valve orifice, wherein the plug has a prosthetic valve inside with an inflow end and an opposite outflow end.

Preferably, the plug comprises a stent, a covering membrane and a prosthetic valve. The stent has a shape of one or combination of a tubular shape, a conical shape or a spherical shape. The stent is of a mesh structure therefore is compressible and expandable. The covering membrane covers at least a portion of an inner and/or outer surface of the stent. The prosthetic valve is attached on inside of the stent.

Preferably, the stent is of a lattice structure with rhombic and/or hexagonal meshes, and the densities of the rhombic and/or hexagonal lattice structures gradually decrease from the middle to both ends; prosthetic valves are sewn in the position on the stent with dense mesh of rhombic and/or hexagonal lattices.

Preferably, the stent is formed by a laser cutting technique, an integral 3D printing technique or from woven/braided crossing filament.

Preferably, the stent is made of a super elastic alloy material having a shape memory property, preferably a Ni—Ti alloy; the covering membrane is made of any one of polyethylene material, artificial blood vessel material, polyurethane material, porcine, bovine or other animal pericardium material; the prosthetic valve is made of porcine, bovine or other animal valve, biological tissue material, polymeric material, or can be tissue engineered valve.

Preferably, the stent is of a meshed cylindrical tube, a truncated cone tube, or one or a combination of a cone, a sphere, a hemisphere, and an ellipsoid.

Preferably, the stent is in the shape of an inverted truncated cone tube and/or an inverted cone; the stent has a total length of 20-80 mm and an inner diameter of 0-50 mm.

Preferably, the stent is in the shape of a truncated cone tube or a cone, wherein the inner diameter of the stent from proximal end to distal end gradually increases then decreases gradually; the stent has a total length of 20-80 mm and an inner diameter of 0-50 mm. The inner diameter can vary in a range of 0-50 mm.

Preferably, the stent is in a truncated cone tubular shape having a mesh structure, wherein the inner diameter of the truncated cone tubular stent from proximal end to distal end decreases gradually; the inner diameter even can decrease to 0 to form a cone.

Preferably, the shape of a stent having a mesh structure from proximal end to distal end is composed of cone A and inverted cone B, and the inner diameter of the bottom surface of cone A and the inner diameter of the bottom surface of inverted cone B are the same, wherein the length of cone A is smaller than the length of inverted cone B.

Preferably, a fixation device with a prosthetic valve inside, configured to anchor the plug (referred to as valve-in-plug in descriptions below) comprises a hollow sleeve connecting the inflow end or proximal end of the valve-in-plug, and a guide wire passing through the prosthetic valve and the hollow sleeve; the distal end of the guide wire is provided with an anchor; and the proximal end of the guide wire and the proximal end of the hollow sleeve anchors and locates the valve-in-plug by adjusting the relative position through a control handle. After implantation of the device, the proximal ends of the guide wire and of the hollow sleeve is secured and placed inside the body.

Preferably, the anchor is secured on the myocardium near the apex of the right ventricle; the anchoring hook is made of shape memory alloy, preferably Ni—Ti alloy.

Preferably, the hollow sleeve passes through the valve-in-plug and prosthetic valve, forming a channel for the guide wire sliding inside of the valve-in-plug.

In a second aspect of the present invention, as a technical solution of the present disclosure it provides a method for implanting a device for treating tricuspid regurgitation, characterized with the following steps:

(1) an incision is made in the subclavian vein or jugular vein; a guide wire with an anchoring hook attached at a distal end is inserted inwardly from the incision towards the right ventricle, and the anchoring hook is then secured to the myocardium near apex of the right ventricle;

(2) a compressible and expandable valve-in-plug having an inflow and an outflow end is then compressed into a retractable sheath, tube, or the like, deployment catheter, and the valve-in-plug is delivered along the guide wire to the native tricuspid valve orifice; the valve-in-plug is released and expanded automatically; the sheath, tube, or the like, deployment catheter is withdrawn; a proximal end of the valve-in-plug is connected to a hollow sleeve, and a guide wire passes through the hollow sleeve;

(3) the position of the valve-in-plug at the tricuspid valve orifice is adjusted by sliding the hollow sleeve along the guide wire then secured and locked;

(4) the proximal end of the guide wire and the proximal end of the hollow sleeve are buried in body tissue after the implantation of the valve-in-plug device for treating tricuspid regurgitation.

In a third aspect of the present invention, the present disclosure provides the use of a device for treating heart valve regurgitation for selected patients from the group consisting of mitral regurgitation and/or tricuspid regurgitation.

The device for treating tricuspid valve regurgitation and method of implanting the same provided by the present disclosure have the following advantages:

(1) during systole when the native tricuspid valve is closed, the valve-in-plug serves as a plug blocking the tricuspid valve leakage orifice and prevent blood regurgitation;

(2) during diastole, the prosthetic valve in the plug opens concomitantly with the native tricuspid valve; therefore, the total effective inflow orifice area is increased against the plug only device to prevent tricuspid stenosis;

(3) the whole device is retrievable after the device has been deployed in position; in case of suboptimal placement, or unsatisfactory results, the device may optionally be withdrawn by retracting the compressible and expandable valve-in-plug through the sheath tube, by retracting the guide wire with the anchoring hook through the sheath tube, etc., to restore the preoperative state;

(4) the device according to the present disclosure is preferably utilized by minimally invasive percutaneous technology and does not require open-heart surgery or thoracotomy, and is suitable for high risk patients.

The concept, specific structure and technical effects of the present disclosure will be further described below with reference to the accompanying drawings to fully understand the objectives, features and effects of the present disclosure.

BRIEF DESCRIPTION OF THE DRAWINGS

FIG. 5B is schematic view of a preferred prosthetic valve stent provided with inner membrane: 5B-1 is a top view, 5B-2 is a front view of 5B-1, 5B-3 is a schematic perspective view, and 5B-4 is a bottom view; wherein 41: a middle part of a truncated cone stent having a rhombic lattice structure, 42, 47: inflow end and outflow end of truncated cone stent having a relatively low density mesh, 43: guide wire; 44: base for connecting the hollow sleeve; 49: inner membrane on the stent.

DETAILED DESCRIPTION

Certain specific details are set forth in the following description and the attached drawings, in order to provide a thorough understanding of various embodiments of the disclosure. A person of ordinary skill in the relevant art will understand that they are capable of practicing other embodiments of the invention without one or more details described herein. Accordingly, applicants are not intended to in any way limit the scope of the appended claims to such details. Although the description of various processes makes reference to the steps and sequences in the following disclosure, the steps and sequences of these steps should not be considered as essential to the practice of all embodiments of the disclosure.

As used herein, the term "proximal" shall mean near the operator (less into the human body) and "distal end" shall mean away from the operator (more into the human body).

As used herein, the term "inflow end" is the end that blood flows in and "outflow end" is the end that blood flows out of.

As used herein, the term "sheath" may also be described as a "catheter", and thus these terms are used interchangeably.

As used herein, the term "network structure" may also be described as a "lattice structure".

The "artificial tissue materials" include tissues that are manufactured by tissue engineering in a laboratory, such as the combination of extracellular matrixes, cells and biologically active molecules as designed. The artificial tissue materials may employ tissue originated from kangaroo, ostrich, whale or any other suitable heterograft or homograft of any reasonable size. The artificial tissue materials also include connective tissue proteins that are employed as the scaffolds of tissue materials (that is, collagen and elastin). In order to strengthen the tissue protein compound, a chemical fixation process can be employed to link proteins.

The patient or subject to be treated according to the disclosure, i.e., the patient or subject having a cardiac valve regurgitation, is a mammal, preferably a human.

The device described in the disclosure and its implantation method is to reduce or block blood flowing from the right ventricle to the right atrium during systole and to allow sufficient blood flowing from the right atrium to the right ventricle during diastole.

Most cases of tricuspid regurgitation are due to dilatation of annulus or tethering of tricuspid valve leaflets due to increased right ventricular volume. During systole, a gap forms between the tricuspid valve leaflets, causing an insufficient closure. The device for treating tricuspid regurgitation according to the present disclosure can reduce the size of the gap; and in some cases, sufficiently eliminate the gap so the native tricuspid regurgitation become mild or trace. In some of the embodiments described herein, by positioning the device between the native tricuspid leaflets to plug the gap. In some of the embodiments described herein, the regurgitation treatment device would not reduce the effective orifice area, allowing adequate blood flow from the right atrium to the right ventricle.

The following description refers to FIGS. 1 to 8. A person ordinally skilled in the art will recognize that the drawings and the description of the drawings are directed to various embodiments of the disclosure, and are not intended to limit the scope of the appended claims to the accompanying drawings and/or description of the drawings, unless required in the context.

Figure 1:
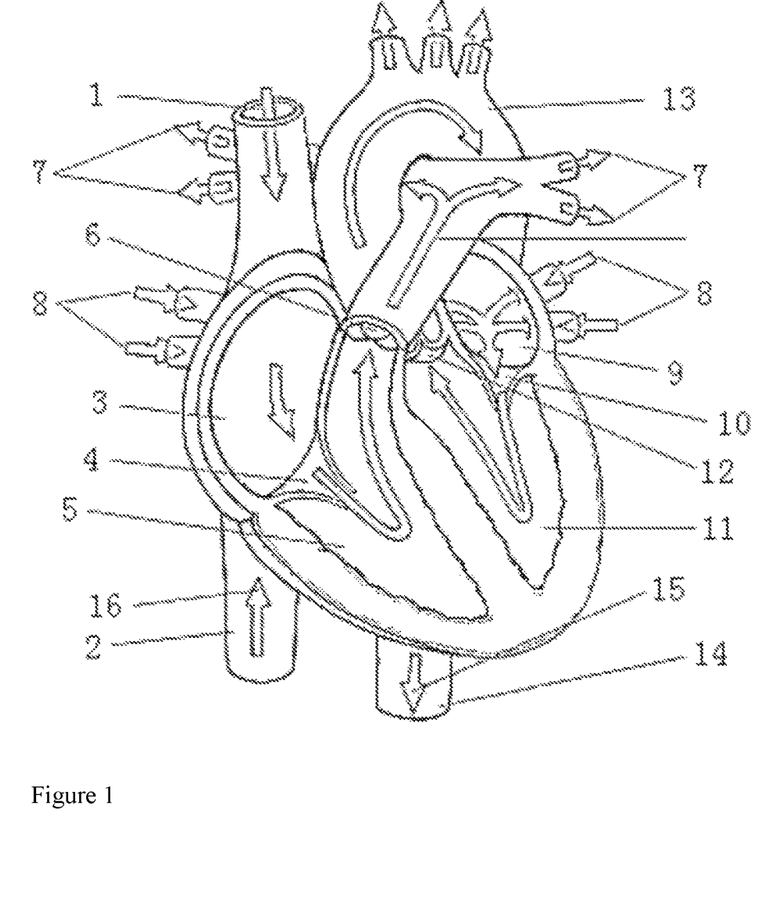
FIG. 1 is a schematic view of the anatomy of the human heart: wherein 1: superior vena cava, 2: inferior vena cava, 3: right atrium, 4: tricuspid valve, 5: right ventricle, 6: pulmonary valve, 7: pulmonary artery, 8: pulmonary vein, 9: left atrium, 10: mitral valve, 11: left ventricular, 12: aortic valve, 13: aorta, 14: descending aorta, 15: oxygenated blood flow direction, and 16: hypoxic blood flow direction.

FIG. 1 is a schematic view of the anatomy of human heart. The tricuspid valve 4 consists of three similar triangular segments or leaflets (anterior, posterior and middle or septal cusp). The base of valve is connected to a fibrous annulus (not shown in FIG. 1) surrounding the atrioventricular orifice and is also interconnected to form a continuous annulus. Tricuspid valve has an atrium surface, which faces the blood flowing from atrium 3 and its ventricular surface faces the wall of ventricle 5; valve cusps connect to the chordae at the tip of the leaflets. As mentioned above, the function of the tricuspid valve is to prevent blood from flowing back into the right atrium 3; the arrow indicates the direction of normal blood flow. Tricuspid regurgitation occurs when tricuspid valve 4 is not sufficiently closed, causing the blood to leak back into the right atrium 3.

In a first aspect, the technical solution of the present disclosure provides a device for treating tricuspid regurgitation, the device comprises a compressible and expandable valve-in-plug, and a valve-in-plug fixation device for anchoring the valve-in-plug to the tricuspid valve orifice. The valve-in-plug has an inflow end, an opposite outflow end, and a prosthetic valve in the valve-in-plug that can open and close. The prosthetic valve is closed when the native tricuspid valve is closed and it opens when the native tricuspid valve opens such that there is a blood flow from the inflow end of valve-in-plug to the outflow end.

Valve-in-Plug

The valve-in-plug can be anchored by the fixation device at the gap of the native tricuspid valve and functions as a plug in the gap. The opening and closing of the prosthetic valve synchronize with the opening and closing of the native tricuspid valve. During systole, the native tricuspid valve is closed, the valve-in-plug blocks the leakage gap of the native tricuspid valve, the prosthetic valve in the valve-in-plug is also closed, effectively reduces the regurgitation; during diastole, the native tricuspid valve opens, the valve-in-plug stays near the position due to the tension from the anchoring device. When the blood flows from the right atrium to the right ventricle, the prosthetic valve inside the valve-in-plug opens at the same time with the native valve so there is blood flow from the inflow end to the outflow end of the valve-in-plug, in addition to blood flow through native valve, to prevent the tricuspid stenosis.

The valve-in-plug is compressible and expandable, the compressed configuration being a delivery configuration when the valve-in-plug is being delivered via a catheter, and the expanded configuration is the working configuration of the valve-in-plug after having been implanted into human heart. Some embodiments of the present disclosure employ the principle of self-expansion. The device is initially compressed, placed in the sheath, and upon reaching a predetermined position in the native tricuspid valve orifice, to be released and self-expanded to its originally designed working configuration and is fixed by the anchoring device into the heart.

In some embodiments of the present disclosure, the valve-in-plug comprises a stent, membranes and a prosthetic valve; the stent has a tubular shape or similar, having a lattice structure and is compressible and expandable; the membrane covers at least a portion of an inner and/or outer surface of the stent; the prosthetic valve is attached within the stent. The membrane is hemostatic.

Stent

The stent according to the present disclosure is a compressible and expandable hollow structure that allows blood flow in the center area, which also serves as the supporting structure for a prosthetic valve inside to form a valve-in-plug.

In some embodiments of the present disclosure, the valve-in-plug is in a shape of a tube, a cone or a sphere or combinations of such shapes. The stent is in a shape of a cone, a truncated cone, a sphere, a hemisphere, and an ellipsoid or any combination of such shapes.

For example, it can be a cylindrical tube configuration, or a combined configuration of cylindrical tube and a truncated cone or a cone. The stent can be in a shape similar to the combination of a hemisphere and a cylinder.

Preferably, the stent is in the shape of a truncated cone tube or a cone, the inner diameter of the stent decreases gradually from proximal end to distal end. The truncated tubular or conical stent serves as a support structure for the valve-in-plug, and will better fit with the native tricuspid valve when being implanted in the tricuspid orifice, therefore beneficial to reduce regurgitation.

In some embodiments of the present disclosure, the stent has a rhombic and/or hexagonal lattice. The shape of the mesh can be of any shape that meets the functional requirements and allows compression and expansion. Preferably, the stent is a lattice structure with rhombic and/or hexagonal meshes.

In some embodiments of the present disclosure, the stent lattice density can be uniform or not. Preferably, the density of the stent lattice (or mesh) is high in the middle and low on both ends, changing gradually. The middle part having a relatively high density will facilitate the sewing of the prosthetic valve and/or membrane to obtain stable support for prosthetic valve; the membrane will help to prevent perivalvular leakage.

The method for manufacturing the stent in the present embodiment is preferably laser cut technique. In other preferable embodiments, an integral 3D printing technique can be utilized, or it can be manufactured by weaving/braiding or similar methods.

The stent can be made of metallic material but can also be made of other materials having strong supporting strength. Preferably the stent is made of a shape memory alloy material, such as Ni—Ti alloy.

The valve-in-plug in the present embodiment can be designed with different sizes according to patient conditions, specifically related to the sizes of right atrium/ventricle and the native tricuspid orifice.

In some embodiments, the valve-in-plug can be designed to have an inner diameter of 0-50 mm and a total length of 20-80 mm.

In some embodiments, the valve-in-plug can be designed to have an inner diameter in a range of 5-45 mm and a total length of 20-80 mm.

In some embodiments, the valve-in-plug can be designed as a cylindrical tubular stent having an inner diameter of 0-40 mm or 5-35 mm and a length of 20-80 mm.

Figure 4:
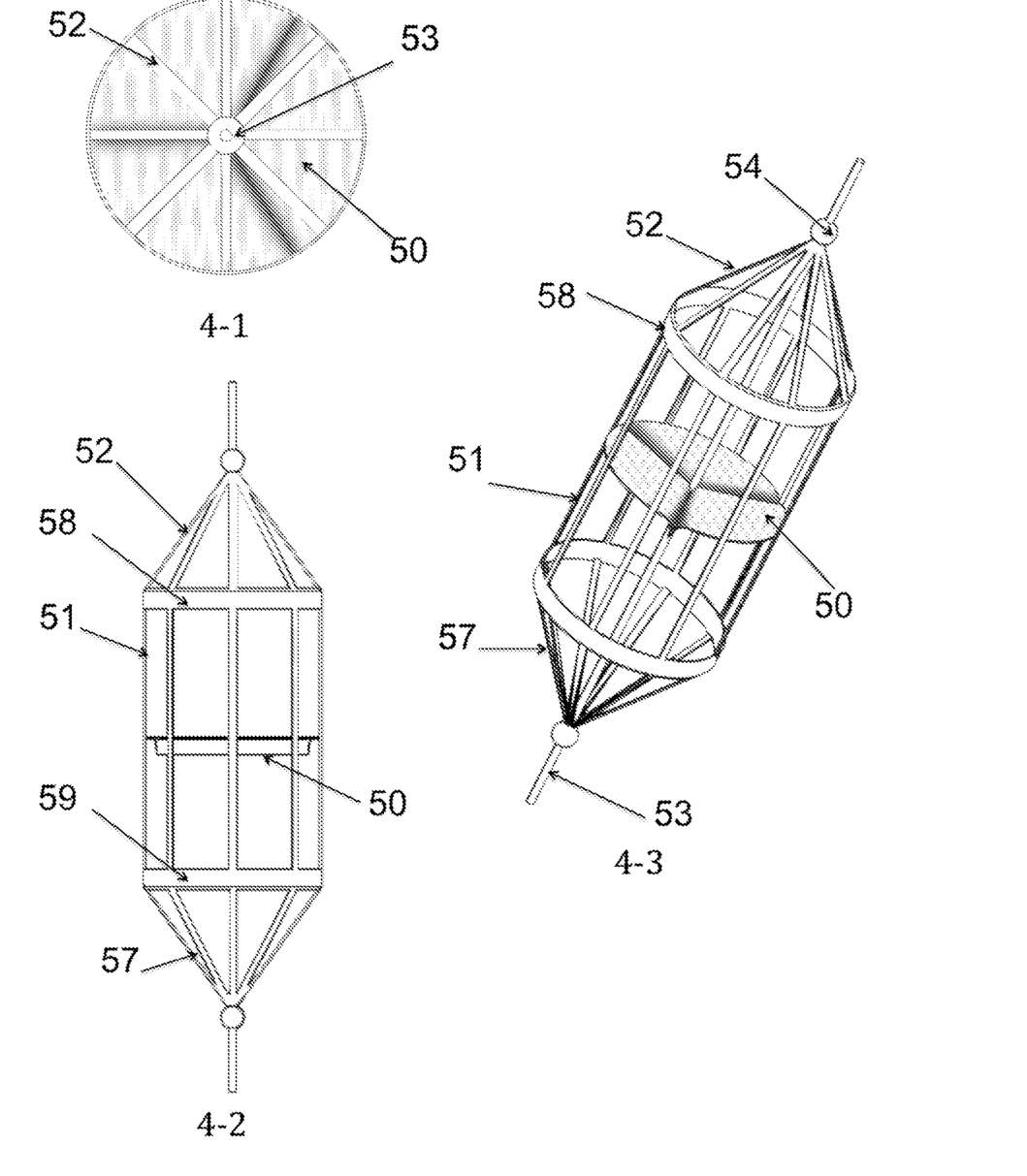
FIG. 4 is schematic view of a preferred stent with a prosthetic valve: 4-1 is a top view, 4-2 is a front view of 4-1, 4-3 is a perspective schematic view of 4-1; wherein 51 is a middle part of a cylindrical tubular stent, 52, 57 are connectors (inflow end and outflow end) of the conical lattice stent, 53 is guide wire, 54 is the base for connecting the hollow sleeve, 50 is prosthetic tri-leafleted valve, 58, 59 are soft hoop-shaped parts.

In some embodiments, the stent of valve-in-plug can be designed as having a cylindrical tube with rectangular lattice in the middle, and a cone with triangle lattice at both ends, the middle and the two ends are connected by soft band, as shown in FIG. 4. In addition, different parts having different types of lattice can be connected by components made of soft band, to enable an expandable and compressible feature.

Figure 3A:
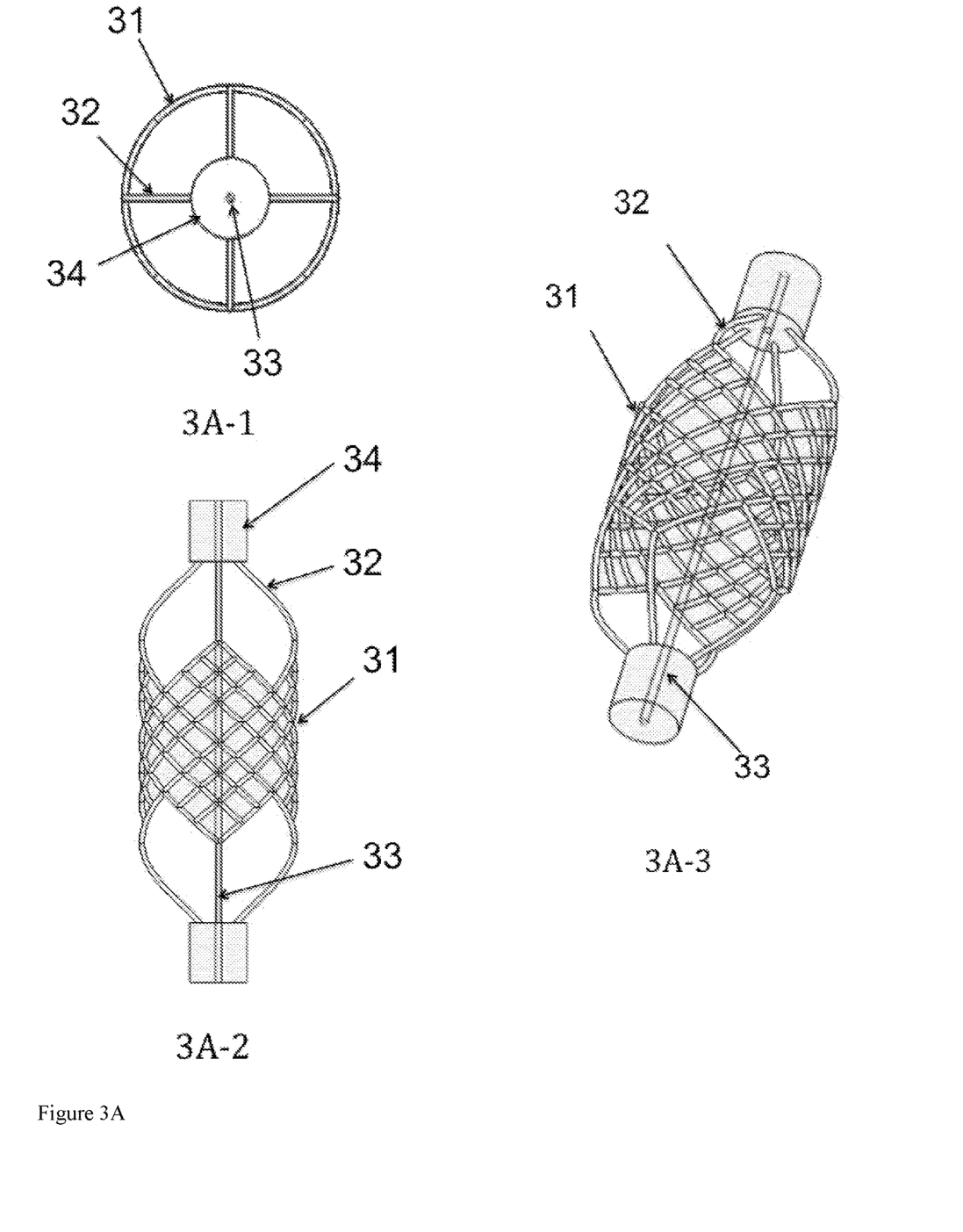
FIG. 3A is schematic view of a preferable valve-in-plug device: 3A-1 is a top view, 3A-2 is a front view of 3A-1, 3A-3 is a three-dimensional schematic view of 3A-1; wherein 31: a middle part of a cylindrical tubular stent having a rhombic lattice structure, 32: end of a truncated cone stent having a relatively low density mesh, 33: guide wire, 34, 35: bases, and 34 is for connecting a hollow sleeve.

In some embodiments, the stent of valve-in-plug can be designed in a tubular shape with a truncated cone at each end and a cylinder in the middle. The stent having a cylinder in the middle has an inner diameter of 5-50 mm and a length of 20-80 mm, and the inner diameter gradually shrinks to two ends to 5-40 mm. A preferable embodiment is shown in FIG. 3A, wherein 31 is a middle part of a cylindrical tubular stent having a rhombic lattice structure, 32 is the end of a truncated cone stent having a relatively low density mesh, 33 is a guide wire, cylinders 34, 35 are bases for fixing the stent having a lattice structure, and cylinder 34 located at inflow end is for connecting a hollow sleeve.

In some embodiments, the valve-in-plug is designed as a cone stent, its proximal end is a conical base, having a diameter of 10-50 mm, the inner diameter gradually decreases to the distal end and its total length is 20-80 mm. The conical base also has crossing lattice convenient for connecting a valve-in-plug fixation device.

In some embodiments, the valve-in-plug stent is designed as a truncated cone, its proximal end (inflow end) is circular, having an inner diameter of 5-50 mm, the inner diameter gradually decreases to the distal end (outflow end) to be 5-40 mm and its total length is 20-80 mm.

Figure 3B:
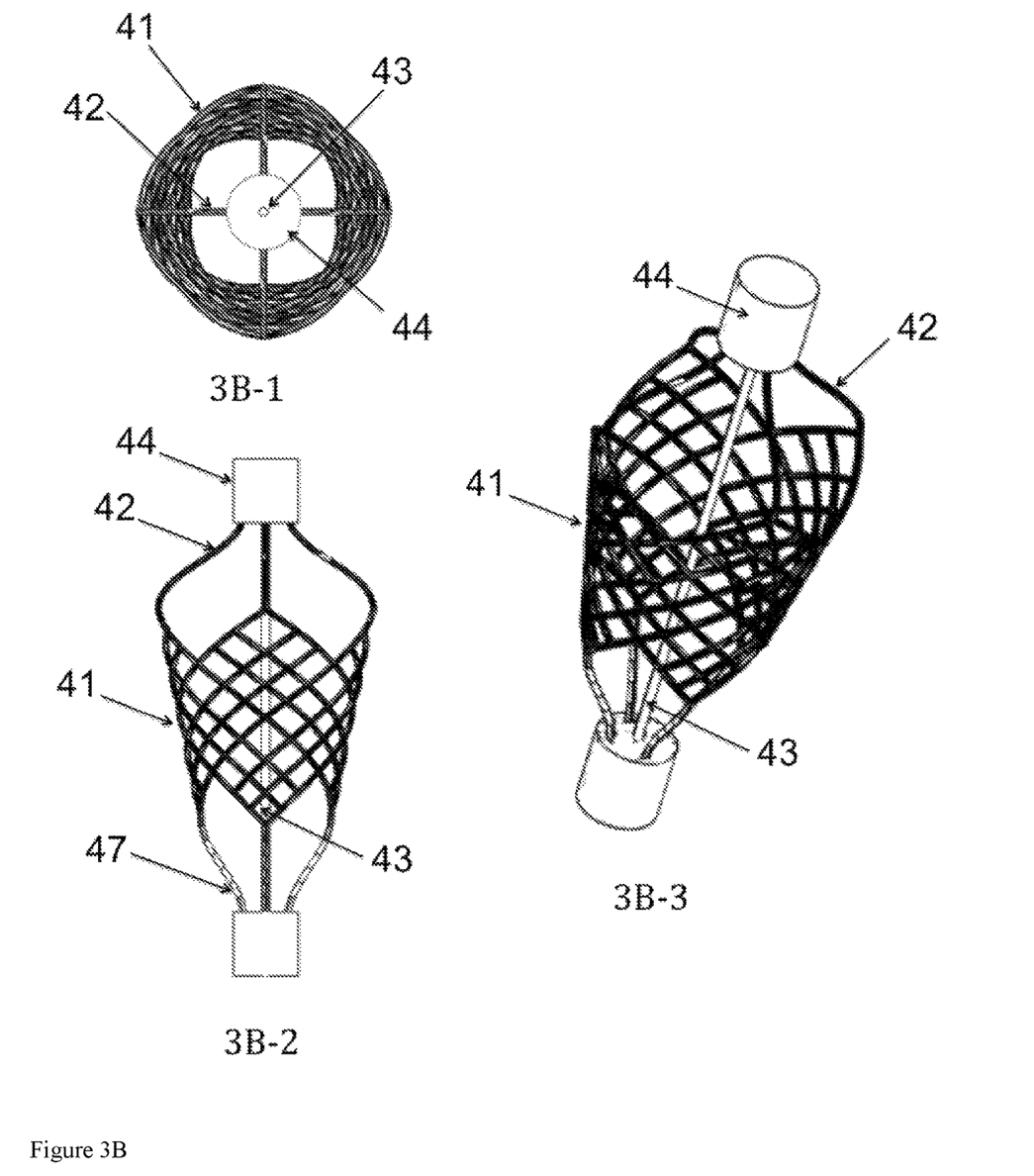
FIG. 3B is schematic view of a preferable valve-in-plug device: 3B-1 is a top view, 3B-2 is a front view of 3B-1, 3B-3 is a three-dimensional schematic view of 3B-1; wherein 41: a middle part of a truncated cone stent having a rhombic lattice structure, 42: an inflow end of truncated cone stent with a relatively low density mesh, 47: outflow end of truncated cone stent having a relatively low density mesh, 43: guide wire, 44: base for connecting the hollow sleeve.

In some embodiments, the stent of valve-in-plug is designed similar to the combination of truncated cones; a preferable embodiment is shown in FIG. 3B, 3B-1 is a top view, 3B-2 is a front view of 3B-1, 3B-3 is a three-dimensional schematic view of 3B-1; wherein 41 is a middle part of a truncated cone stent having a rhombic lattice structure, 42 and 47 are ends (inflow end and outflow end) of truncated cone with a relatively low density mesh, and when the valve-in-plug is implanted into the native tricuspid valve, 42 is proximal end, 47 is distal end, 43 is a guide wire, 44 is a base for fixing and connecting the hollow sleeve. 41, 42, 47 in the figure constitute a stent similar to the combination of truncated cones, the inner diameter gradually increases then gradually decreases from the proximal end to the distal end.

A specific stent size can be provided according to the patient's heart. The preferred sizes are as follows: the narrowest inner diameter is 10-15 mm, the widest inner diameter is 35-45 mm, and the total length is 50-80 mm.

In some preferable embodiments, such as the shape of the stent as shown in FIG. 3B, the stent can be divided into three parts from inflow end to outflow end; the first part of a cone stent has an inner diameter increasing from 3-6 mm to 15-50 mm and a length of 5-10 mm; the first part of the cone may be of several arc lattice line branches and extends to the second part of truncated cone , the inner diameter is decreased from 15-50 mm to 0-40 mm and the length is 20-60 mm; and then through the arc lattice line it is gradually transformed to the third part wherein the inner diameter is changed from 0-40 mm to 3-5 mm and the length is 0-10 mm. The rhombic lattice of the first part and the third part are of lower density than the second part.

Prosthetic Valve

The prosthetic valve in the valve-in-plug described in the present disclosure can open and close simultaneously with the native tricuspid valve. The prosthetic valve is sewn inside the stent, preferably sewn to the stent membrane.

The prosthetic valve may be a tri-leaflet valve, or a bi-leaflet valve or a quardro-leaflet valve. Tri-leaflet valve is preferred in the present disclosure, the leaflets are fixed on the lattice of the stent; the free edge portions can be completely coaptated together.

In some embodiments, the stent with a prosthetic valve, shown in FIG. 4, the prosthetic valve is sewn axially inside the stent perpendicular to the stent to form a cross-section, wherein 51 is a middle part of a cylindrical tubular stent, 52 and 57 are ends of a conical stent, 53 is a guide wire, 54 is a spherical part for connecting the hollow sleeve, 50 is a tri-leaflet valve, 52 is the proximal end (inflow end), 57 is the distal end (outflow end), 58 and 59 are soft bands. The soft bands are for connecting the proximal and distal conical parts to a cylindrical tubular part in the middle, respectively. The soft band may be of the same material as the membrane according to the present disclosure, preferably using pericardial tissue. The stent in the present embodiment has rectangular lattice in the middle part and triangular lattice at the two end parts. These parts are connected by soft bands to allow compression and expansion during catheterization.

The closed state of a tri-leaflet valve 50 is as shown in FIG. 4-3. When blood flows in from the inflow end, the valve leaflet 50 is opened toward the distal end (outflow end) 57; that is, the three leaflets of the valve are folded to the distal end 57 to allow blood flow. When blood flows into the stent from the distal end 57, the tri-leaflet valve 50 is in a closed state, blocking back flow of blood. The stent shown in FIG. 4 has inner diameter gradually decreasing at the inflow end and the outflow end, so it can be compressed. Although a membrane is not shown in the figure, a membrane is preferably sewn on the middle part of stent 51, and preferably on both the inner and outer peripheral surfaces of the stent 51.

In some embodiments, the prosthetic valve may be made of an animal (preferably pig) valve, porcine or bovine pericardium, or of a biological tissue material, a polymer material or a tissue engineered valve.

The position where the prosthetic valve is attached (sewn) inside the stent is not particularly limited; the prosthetic valve is preferably sewn in one example at the part of higher density mesh, and in another example, preferably in the middle of the stent.

Membrane

The membrane of the present disclosure serves to ensure the sealing of the valve-in-plug. The membrane on the inner and/or outer surface of the stent can prevent blood flow through the mesh of the stent, thus preventing perivavular leakage.

The membrane may be provided between the stent and the prosthetic valve, and may also cover the outer surface of the stent. Most preferably, a membrane is provided at the outer surface of the stent and between the stent and the prosthetic valve (i.e., on the inner surface of the stent), to form double membrane. The membrane covers at least a part of the inner and/or outer surface of the stent.

The membrane is to prevent peripheral leakage from the prosthetic valve. It also blocks blood flow around the exposed stent mesh components thus reduces or eliminates the potential of thrombosis at the stent. The membrane can be sewn onto the stent. If a membrane is sewn on inner surface of the stent, the prosthetic valve can be sewn to the membrane and stent at the same time.

The membrane can be made of polyethylene material, tissue engineered material, prosthetic blood vessel material, polyurethane material, porcine or bovine pericardium or the like, and can also be made of polytetrafluoroethylene, woven fabric, non-woven fabric, woven polyester and the like.

Figure 5A:
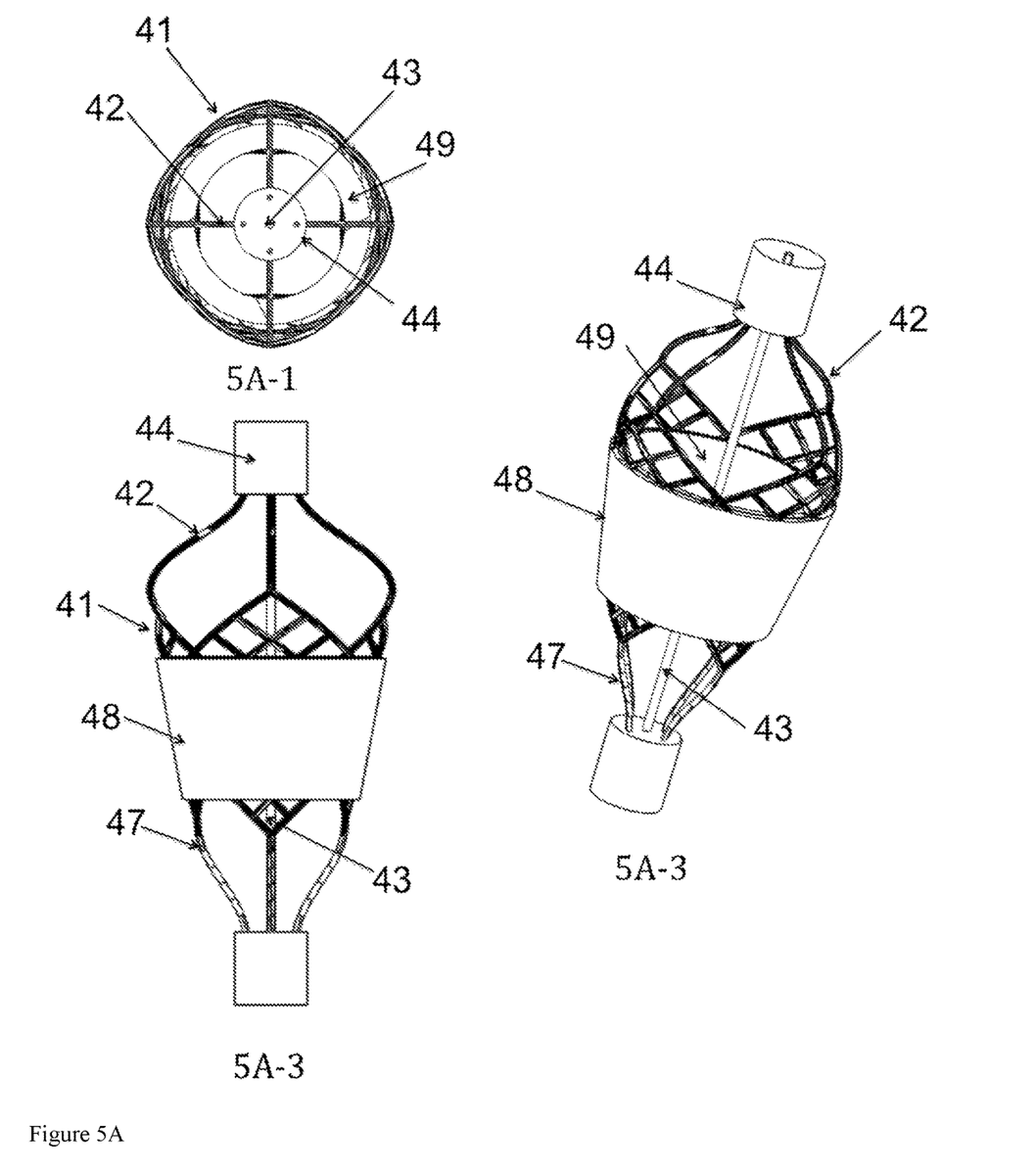
FIG. 5A is schematic view of a preferred prosthetic valve stent provided with an inner and outer membrane: 5A-1 is a top view, 5A-2 is a front view of 5A-1, and 5A-3 is a schematic perspective view of 5A-1; wherein 41: a middle part of a truncated cone stent having a rhombic lattice structure, 42, 47: inflow end and outflow end of truncated cone stent having a relatively low density mesh, 43: guide wire; 44: base for connecting the hollow sleeve; 48: outer membrane on the stent, 49: inner membrane on the stent.

In some preferred embodiments, as shown in FIGS. 5A and 5B, the membranes can be sewn to the inner and outer surfaces of the middle part of the stent or may be sewn only on the inner surface or may be sewn only on the outer surface.

FIG. 5A is a schematic view of a preferred valve-in-plug provided with an inner and outer membrane: 5A-1 is a top view, 5A-2 is a front view of 5A-1, and 5A-3 is a schematic perspective view of 5A-1; wherein 41: a middle part of a truncated cone stent having a rhombic lattice structure, 42, 47: inflow end and outflow end of truncated cone stent having a relatively low density mesh, 43: guide wire; 44: base for fixing the stent and for connecting the hollow sleeve; 48: outer membrane, 49: inner membrane.

FIG. 5B is a schematic view of a preferred valve-in-plug provided with an inner membrane: 5B-1 is a top view, 5B-2 is a front view of 5B-1, 5B-3 is a schematic perspective view, and 5B-4 is a bottom view; wherein 41: a middle part of a truncated cone stent, 42, 47: inflow end and outflow end of a truncated cone stent of relatively lower density mesh, 43: guide wire; 44: base for fixing the stent and for connecting the hollow sleeve; 49: inner membrane.

Valve-in-Plug Fixation Device

The valve-in-plug fixation device is for reliable anchoring and positioning of the valve-in-plug.

In some preferable embodiments of the present disclosure, the valve-in-plug fixation device comprises a hollow sleeve connecting the proximal end of the valve-in-plug and a guide wire passing through the center of prosthetic valve and the hollow sleeve.

Figure 7:
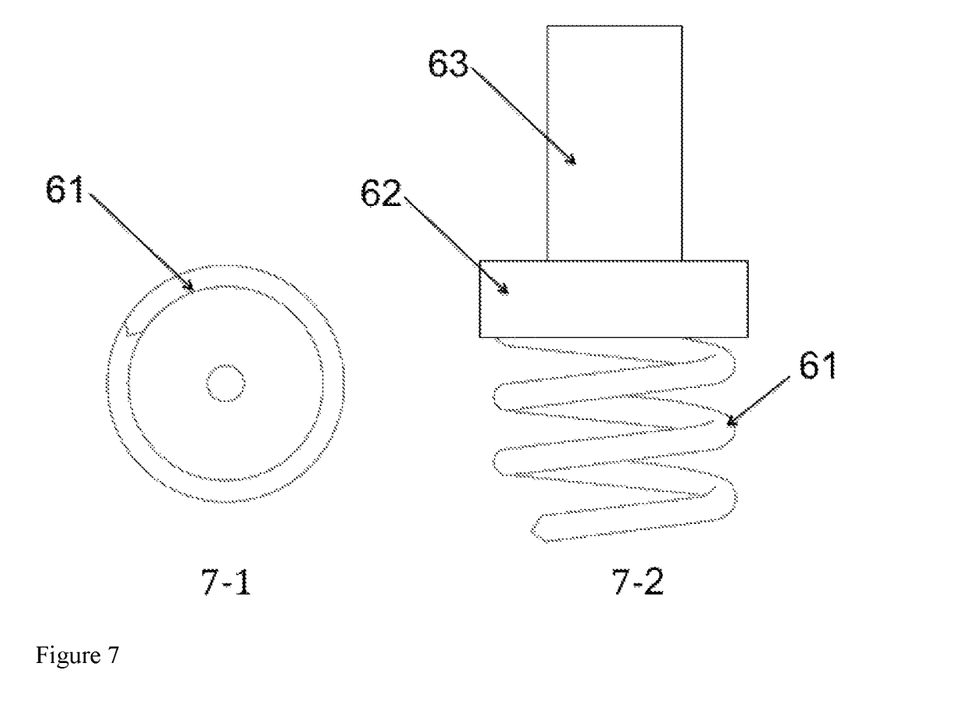
FIG. 7 is schematic view of the spring shaped anchor of the preferable device: 7-1 is a bottom view, 7-2 is a front view of 7-1; wherein 61: a helical spring anchor, 62: anchoring base, 63: an element for connecting the guide wire.

The distal end of the guide wire is attached to an anchor. The anchor can be designed to have a shape similar to a hook, which can be compressed into the sheath before delivery. After reaching the position, the anchor is pushed out so that the hook claw is inserted into the ventricular wall. A preferable anchoring position is the myocardium near the apex of right ventricle. The anchor can also be selected from other types, exemplified by the spring claw as shown in FIG. 7. Optionally, the anchor is connected to the guide wire through a screw or a wedge slot.

When implanting the valve-in-plug of the present disclosure, firstly, the guide wire with an anchor at a distal end is fixed in the ventricle, then the valve-in-plug is delivered by sliding the hollow sleeve along the guide wire. The relative position of the hollow sleeve to guide the wire is controlled through an handle, and since the hollow sleeve is connected to the proximal end of valve-in-plug, the position of valve-in-plug can be adjusted through the relative movement of the hollow sleeve to the guide wire. After the valve-in-plug is at the right position, the proximal end of the guide wire and the proximal end of the hollow sleeve can be fixed in the subclavian tissue pouch, which is similar to the method of fixing a pacemaker, it may also allow future withdrawal and adjustment of the position of the valve-in-plug.

The hollow sleeve and the valve-in-plug may be connected by a screw thread or a wedge slot.

The inner diameter of the hollow sleeve should be large enough to allow the guide wire to pass through and slide, the wall thickness of the sleeve should be large enough to withstand the force on the valve-in-plug. Preferably, the hollow sleeve has an inner diameter of 1-3 mm. As shown in FIG. 3A, the hollow sleeve may be connected to the inflow end base 34 and may be connected by a screw thread or a wedge slot.

In some preferred embodiments of the present disclosure, the hollow sleeve may also be through the valve-in-plug, so form a channel inside the valve-in-plug in which the guide wire is sliding through the valve-in-plug.

In some preferred embodiments of the present disclosure, the anchor is preferably made of a shape memory alloy, such as Ni—Ti alloy. This alloy may also be processed so that its transition temperature is near body or body acceptable temperature, and self-expansion can be initiated when the transition temperature is reached. In some preferred embodiments of the present disclosure, the hollow sleeve is made of a polymer material, such as polyurethane or other implantable materials.

The valve-in-plug of the present disclosure may be surgically implanted or may be delivered by a transcatheter method. In the preferred transcatheter method, the valve-in-plug is loaded into a suitable delivery catheter where it is compressed inside a retractable sheath, tube or the like. The delivery catheter is inserted into the diseased tricuspid valve. When treating tricuspid regurgitation, the valve-in-plug is loaded in a compressed state and delivered through the superior vena cava via the jugular vein, then into the right atrium, and expanded after reaching the native tricuspid orifice. Alternatively, the valve-in-plug, can be delivered into the inferior vena cava via the femoral vein, then into the right atrium.

Preferably, the vavled plug of the present disclosure is implanted from the opening in the subclavian vein or jugular vein via a catheter.

Figure 2:
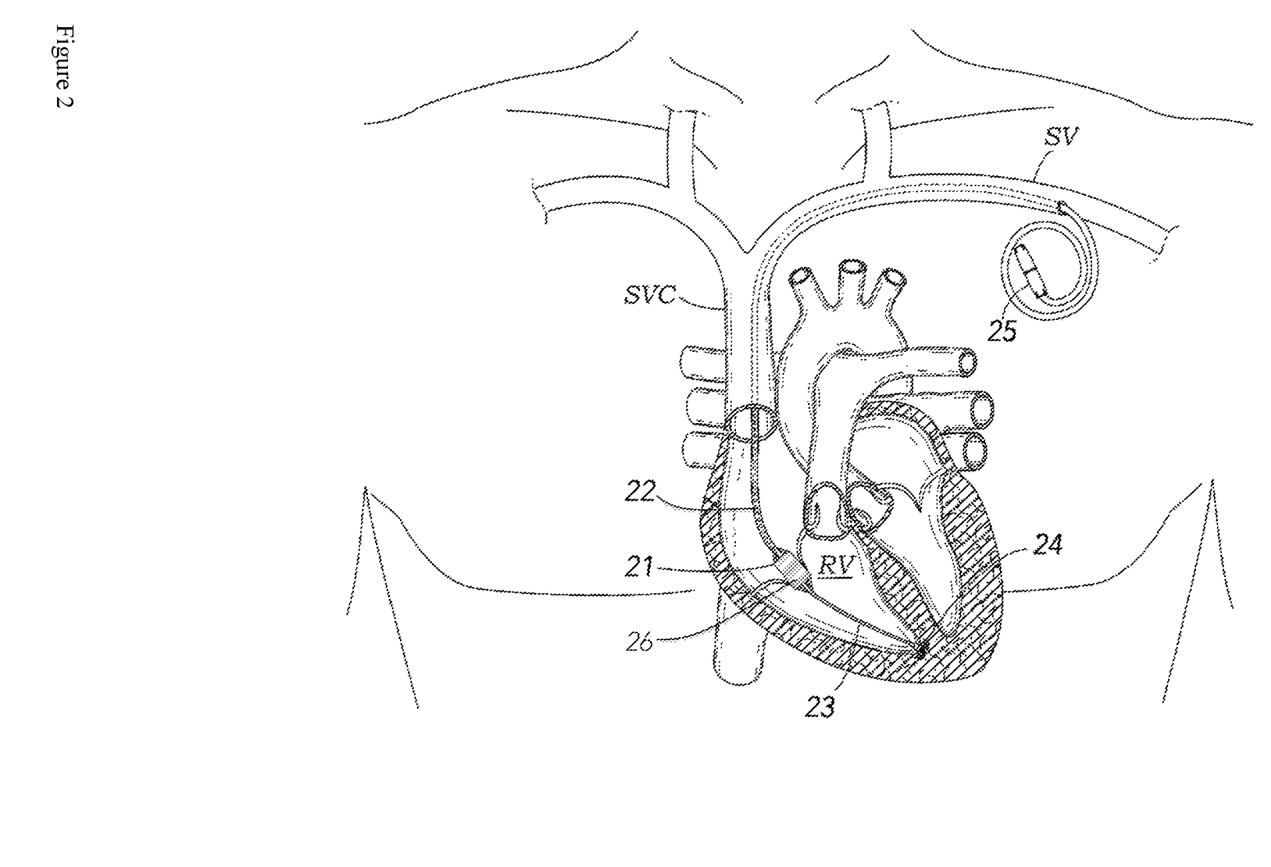
FIG. 2 is a schematic view showing the correct placement of the device in the heart according to one embodiment of the present disclosure, SVC: superior vena cava, RV: right ventricle; 21: valve-in-plug; 22: hollow sleeve; 23: guide wire; 24: anchoring hook, 25: in vitro control device, 26: bushing that wraps around the outer periphery of the valve-in-plug stent.

FIG. 2 is a schematic view showing the correct placement of the valve-in-plug, according to one preferable embodiment of the present disclosure, SVC: superior vena cava, RV: right ventricle; 21: valve-in-plug; 22: hollow sleeve; 23: guide wire; 24: anchor, 25: external control handle, 26: membrane that wraps around the outer surface of the valve-in-plug. In FIG. 2, the valve-in-plug according to the present disclosure is in the expanded state, and the valve-in-plug 21 is exactly located at the native tricuspid orifice. The stent of the valve-in-plug is composed of a combination of a cone and a cylindrical tube, its outer surface is covered with a membrane 26, the proximal end of the valve-in-plug is connected to the hollow sleeve 22, and a guide wire 23 is in the hollow sleeve 22, the distal end of guide wire 23 is connected to an anchor 24, and the anchor 24 has been fixed near the apex of right ventricle. The proximal end of hollow sleeve 22 and guide wire 23 can be adjusted and fixed in position at the external control handle 25, to adjust the position of valve-in-plug 21. The valve-in-plug 21 has a prosthetic valve sewn inside the stent (not shown in FIG. 2, see FIG. 8 for details).

Figure 6:
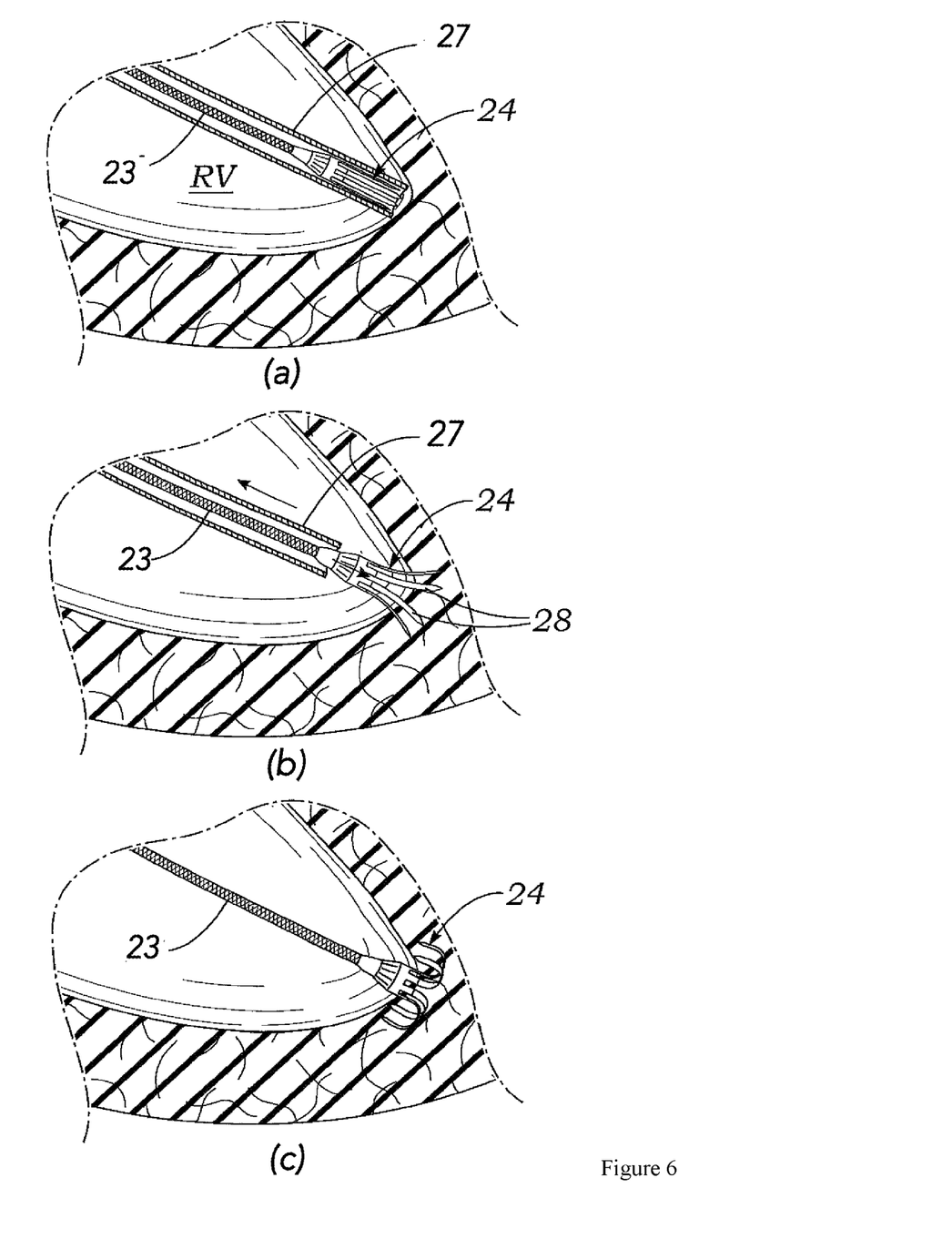
FIG. 6 is a schematic view of anchor delivery for the preferred device: (a)→(b)→(c), 23: guidewire, 24: anchoring hook, 27: sheath, 28: hook of the anchor.

FIG. 6 is a schematic view of anchor delivery for the preferred device as shown in FIG. 2: (a)→(b)→(c), wherein 23: guidewire, 24: anchor, 27: sheath for compressed anchor, 28: self-expanded hook claw on the anchor. Before delivery, the anchor 24 can be compressed in the sheath tube 27. After reaching the implant position, the anchor 24 is pushed out so that the hook claw 28 can be inserted near the apex of right ventricle. After the hook claw 28 is inserted, it restores the preset bent shape and thus fixes the position of the guide wire. The reversed procedure can be used to withdraw the anchor 24. FIG. 7 shows another design of optional anchor, which is a helical spring, having features of screw-in and out, and can also be fixed near the apex of right ventricle.

Figure 8:
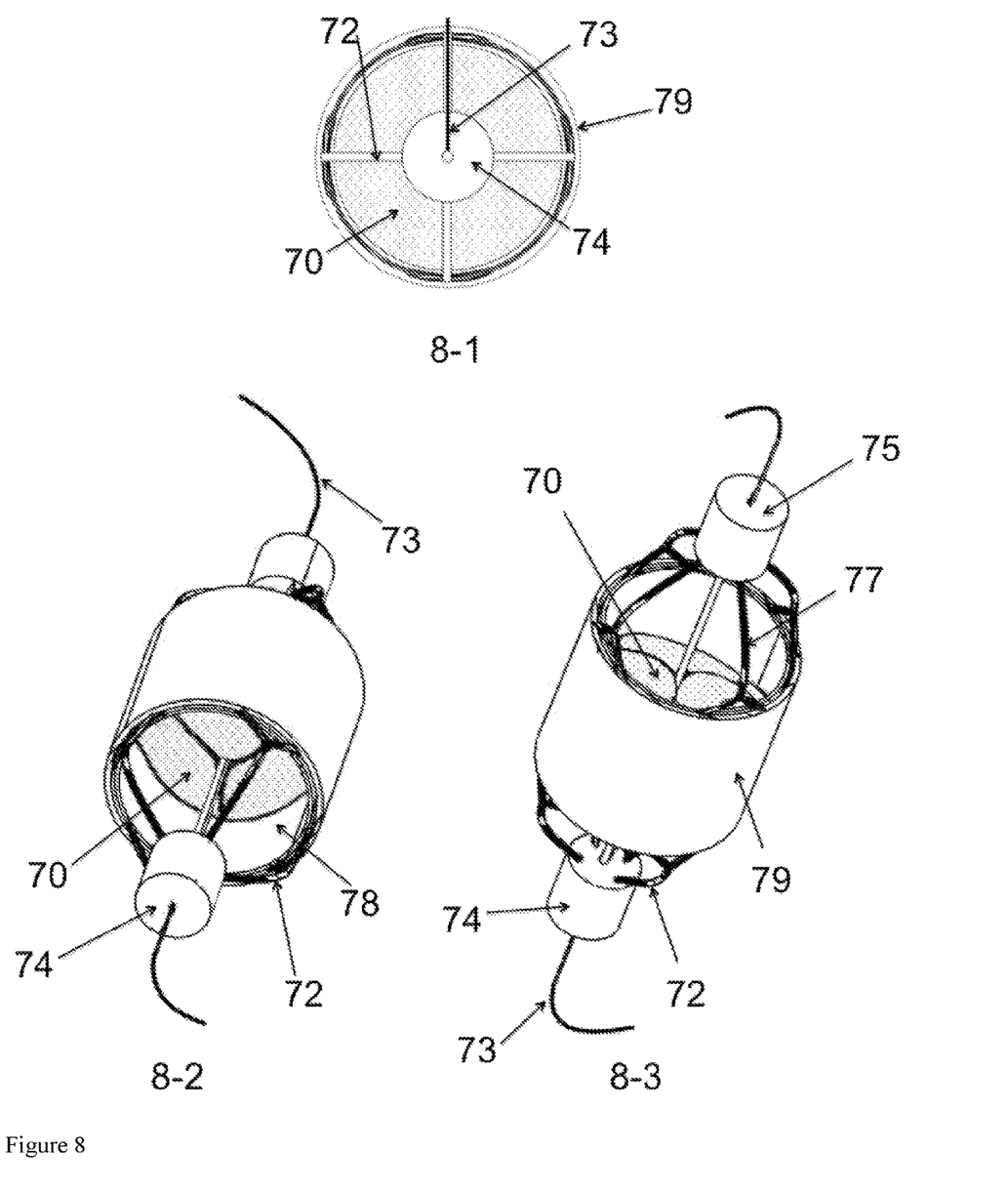
FIG. 8 is schematic view of preferable valve-in-plug provided with internal and external membranes and a prosthetic valve: 8-1 is a top view, 8-2 and 8-3 are perspective views of different angles; wherein 70: a prosthetic tri-leaflet valve, 72: inflow end of a truncated cone stent having a relatively low density mesh, 77: outflow end of a truncated cone stent having a low density mesh, 73: guide wire, 74, 75: base, 74 is also used to connect the hollow sleeve; 79: outer membrane on stent, 78: inner membrane on stent.

FIG. 8 is a schematic view of a preferable valve-in-plug provided with inner/outer membrane and a prosthetic valve as shown in FIG. 2: 8-1 is a top view, 8-2 and 8-3 are perspective views of different angles; wherein 70: a trileaflet prosthetic valve, the middle of the stent is a cylindrical tubular structure having a rhombic lattice (not shown in the figure, see FIG. 3A), 72: inflow end of a truncated cone stent having a relatively low density mesh, 77: outflow end of a truncated cone stent having a relatively low density mesh, 73: guide wire (corresponding to 23 in FIG. 2), 74, 75: base for fixing the stent, 74 is also used to connect the hollow sleeve; 79: outer membrane (corresponding to 26 in FIG. 2), 78: inner membrane.

In some embodiments of the present disclosure, a "visualization element" may be attached to the device to monitor the proper placement of the vavled plug. For example, the optional visualization element can be a radiopaque marker comprising any suitable material, such as, for example, gold, tantalum, platinum, or a combination thereof.

In a second aspect, the technical solution of the present disclosure provides a method for implanting a device for treating tricuspid regurgitation, which comprises the following steps:

(1) an incision is made in the subclavian vein or jugular vein, the guide wire with an anchor attached at a distal end is extended from the incision towards the right ventricle, and the anchor is fixed to the myocardium near the apex of the right ventricle;

(2) a compressible and expandable valve-in-plug having an inflow and outflow end is then compressed into a retractable sheath/tube, or the like, through the delivery catheter, and the valve-in-plug is slided along the guide wire to the native tricuspid valve orifice, the valve-in-plug is then released and expanded automatically, the sheath/tube, and the delivery catheter withdrawn;

(3) the position of the valve-in-plug at the native tricuspid valve orifice is adjusted and fixed by adjusting the relative position of the proximal end of the guide wire and the proximal end of a hollow sleeve;

(4) the relative position of the proximal end of the guide wire and the proximal end of the hollow sleeve is locked then embedded to body tissue to complete the implantation of the device.

Although the embodiments disclosed in the present disclosure are specifically described for tricuspid valve, it is envisioned that these embodiments may be suitable for use with other heart valves. For example, the anchoring structure can be modified to place in different areas, whereas the shape of a valve-in-plug can be modified to fit different valves, such as a mitral valve.

In a third aspect, the technical solution of the present disclosure provides the use of a device for treating heart valve regurgitation, for example, mitral regurgitation and/or tricuspid regurgitation.

The device for treating tricuspid regurgitation described in the disclosure and the implantation method thereof can effectively treat tricuspid regurgitation, also maintain tricuspid inflow, and the device is retractable.

While the disclosure has been described in terms of particular embodiments and applications, based on the teachings, one of ordinary skill in the art may implement alternative embodiments and make additional modification without departing from the spirit of the disclosure or beyond the scope of the disclosure. Accordingly, it should be understood that the drawings and descriptions are provided herein as examples to assist in understanding the present disclosure, and should not be used to limit the scope thereof.

What is claimed is:

1. A device for treating tricuspid regurgitation, comprising
a compressible and expandable plug with a prosthetic valve inside (valve-in-plug),
a fixation device for anchoring the valve-in-plug to block a native tricuspid valve leakage gap,
wherein the valve-in-plug has an inflow and opposite outflow end,
characterized in that,
the valve-in-plug fixation device comprises a hollow sleeve connected to the inflow end or proximal end of the valve-in-plug, and a guide wire passing through the prosthetic valve and the hollow sleeve;
a distal end of the guide wire is provided with an anchor;
and a proximal end of the guide wire and a proximal end of the hollow sleeve are used to position the valve-in-plug by adjusting the relative position by means of a control handle.

2. The device for treating tricuspid regurgitation according to claim 1, wherein
the valve-in-plug that comprises a stent, a membrane and the prosthetic valve;
the stent has a shape of one or combination of a tube shape, a cone shape or a spherical shape, having a lattice structure, and is compressible and expandable;
the membrane covers at least a portion of an inner and/or outer surface of the stent;
the prosthetic valve is sewn within the stent.

3. The device for treating tricuspid regurgitation according to claim 2, characterized in that,
the stent is a lattice structure with rhombic and/or hexagonal meshes, and densities of the rhombic and/or hexagonal lattice structures gradually decrease from a middle part to both ends;
prosthetic valve is sewn to the rhombic and/or hexagonal lattice in the middle part having a higher density than both ends;
the stent is made of a shape memory alloy material, including a Ni-Ti alloy.

4. The device for treating tricuspid regurgitation according to claim 2, characterized in that,
the stent is formed by a laser cutting technique, integral 3D printing technique or by braiding.

5. The device for treating tricuspid regurgitation according to claim 2, characterized in that,
the membrane is made of any one selected from the group consisting of polyethylene material, artificial blood vessel material, polyurethane material, porcine or bovine pericardium material; and
the prosthetic valve is made of porcine or bovine animal valves, biological tissue material, polymeric material, or a tissue engineered valve.

6. The device for treating tricuspid regurgitation according to claim 2, characterized in that,
the stent is in a shape of a truncated cone tube and/or cone;
the stent has a total length of 20-80 mm and an inner diameter of 0-50 mm.

7. The device for treating tricuspid regurgitation according to claim 6, characterized in that,
the anchor is configured to be fixed on a myocardium near an apex of a right ventricle;
the anchor is made of shape memory alloy, including a Ni-Ti alloy.

8. The device for treating tricuspid regurgitation according to claim 6, characterized in that,
the hollow sleeve is passed through the valve-in-plug, forming a channel for sliding the guide wire through the valve-in-plug.

9. A method for implanting a device for treating tricuspid regurgitation, comprising the following steps:
providing a device for treating heart valve regurgitation according to claim 1;
(1) making an incision in subclavian vein or jugular vein, the guide wire with the anchor provided at the distal end is extended from the incision into to a right ventricle, and the anchor is fixed to a myocardium near an apex of the right ventricle;
(2) compressing the compressible and expandable valve-in-plug having the inflow end and outflow end into a retractable sheath/tube, and delivering catheter; and the valve-in-plug is delivered along the guide wire to a native tricuspid valve orifice, the valve-in-plug is then released and expanded automatically, the sheath/tube, or the like, delivery catheter is withdrawn;
(3) adjusting a position of the valve-in-plug at the native tricuspid valve orifice by sliding and changing a relative position of the proximal end the guide wire and the proximal end of the hollow sleeve; and contacting the guide wire with a distal end of the hollow sleeve;
(4) completing implantation of the device for treating tricuspid regurgitation by embedding the proximal end of the guide wire and the proximal end of the hollow sleeve inside the body.

10. A method of using the device for treating heart valve regurgitation according to claim 1, consisting of treating mitral regurgitation and/or tricuspid regurgitation.

\* \* \* \* \*